United States Patent [19]

Hammerslag

[11] Patent Number: 4,560,374

[45] Date of Patent: Dec. 24, 1985

[54] METHOD FOR REPAIRING STENOTIC VESSELS

[76] Inventor: Julius G. Hammerslag, 27011 Calle Esperanza, San Juan Capistrano, Calif. 92675

[21] Appl. No.: 542,850

[22] Filed: Oct. 17, 1983

[51] Int. Cl.⁴ .............................................. A61M 5/00
[52] U.S. Cl. ..................................... 604/49; 128/344
[58] Field of Search ................. 604/49, 8, 9; 128/325, 128/344, 343, 1 R; 3/1.4

[56] References Cited

U.S. PATENT DOCUMENTS 3,042,021 7/1962 Read ....................... 604/8
3,463,158 8/1969 Schmitt et al. .................... 128/334

Primary Examiner—Stephen C. Pellegrino
Attorney, Agent, or Firm—Newton H. Lee, Jr.

[57] ABSTRACT

A synthetic liner is inserted into a blood vessel in the region of a treated stenosis. The liner is composed of a material resistant to the deposition of the fatty matter from the blood so that the build up of a new obstruction to blood flow is inhibited. The liner is tapered to generally conform to the taper or reduction in cross section of the artery in a downstream direction. The material is resilient and has elasticity compatible with the elasticity of the artery.

1 Claim, 3 Drawing Figures

METHOD FOR REPAIRING STENOTIC VESSELS

BACKGROUND OF THE INVENTION

In the treatment of stenosis in the coronary artery system of a patient, coronary artery by-pass surgery is commonly used. More recently, in some cases, it has been found practical to resort to angioplasty procedures, whereby the obstruction can be removed from the arterial system without requiring coronary bypass surgery.

In either case, it has been found to be common that, following the surgery or angioplasty procedure, the tendency is for the stenosis or obstruction to build up in the same arterial section.

As a result of recurrence of the obstruction additional surgery or angioplasty treatments are often required over a period of time. The recurrent treatment could be avoided or reduced if it were possible to prevent the obstruction from recurring at the same general location.

SUMMARY OF THE INVENTION

On the premise that recurrent treatments of the stenotic artery can be minimized if recurrent development of the obstruction can be prevented, the present invention involves the concept that a synthetic liner of material which is resistant to deposition of material from the blood can be inserted into the blood vessel in the region where the obstruction tends to form, thereby reducing the probability of recurrent obstruction to the flow of blood through the blood vessel.

In the practice of the invention a liner of synthetic material is installed in the blood vessel. The liner is preferably tapered or of diminishing cross-section in the direction of blood flow. The taper is selected to substantially equal the typical diminishing cross section of the blood vessels or arteries of the patient. The liner is selected from an insert plastic having substantially the elasticity as the human artery.

In the case of coronary artery by-pass surgery, the liner may be inserted into a vein segment prior to surgically applying the vein segment to a coronary artery being by-passed during coronary by-pass surgery. In the case of angioplasty the liner may be manipulated into position by use of known guide wire structures to locate liner in the selected section of the artery.

My pending application for U.S. Pat. Ser. No. 538,442, filed Sept. 30, 1983, discloses an improved, steerable guide for angioplasty treatments which would be useful in locating a balloon catheter and liner in the desired artery section.

The invention has other advantages which will be apparent from considering the following detailed description of a method of performing the same.

DETAILED DESCRIPTION

Figure 1:
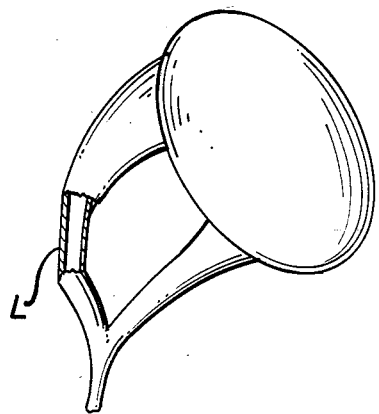
FIG. 1 is a diagrammatic view illustrating a protective sleeve in place.

Reference is first made to FIG. 1. In accordance with the present invention, a thin liner L, say 0.001" in wall thickness is installed in an artery section C at a location where an arterial obstruction has been removed. The liner is slightly tapered so as to closely match the natural tapering or convergence of the arterial passages. With the sleeve in place, it is contemplated that stenosis will not build up again in that same region blocked by the sleeve.

It is contemplated that in most cases the sleeve, once put into place and forced against the interior wall of the artery, will remain in place. Since the artery is elastic and expands and contracts the invention contemplates the use of material having the same or substantially the same elasticity as the artery.

The sleeve may be formed with protuberances on the exterior wall which are calculated to assist in the fixation of the sleeve.

In the case of coronary by-pass surgery, when a section of vein is used to replace the affected artery, the sleeve in accordance with the invention is installed in the vein section during the surgery.

In other cases the sleeve can be put in place by a catheter.

Figure 2:
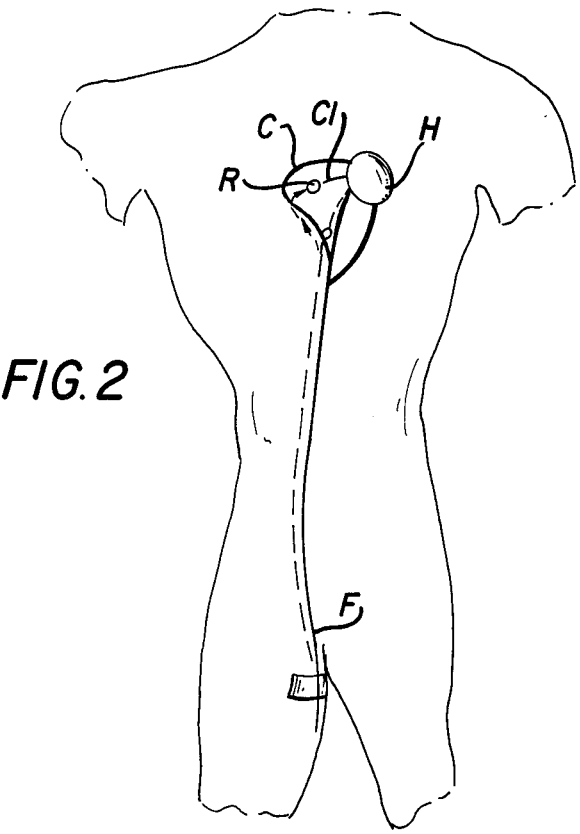
FIG. 2 is a view diagrammatically showing a patient in whose coronary artery is to be placed a protective sleeve in accordance with the invention.

Referrring to FIG. 2, a patient is shown in whose coronary artery system C is to be performed. In general a catheter is to be inserted into the femoral artery F and moved therealong to the coronary artery system, as indicated by the broken arrow, so as to ultimately be situated in artery branch Cl in a restricted section R. To accomplish this the catheter or guide therefor must be caused to negotiate the different angles formed at successive junction between the large femoral artery F and the coronary arteries.

As is well known, the surgeon views the course of the catheter or guide on an x-ray screen, and dye may be injected into the arterial system so that the arteries are better visible. The wires of the guide are also visible, while the balloon catheter has metal rings at the ends of the balloon rendering the position of the balloon clearly visible. When the balloon is situated in the restriction R it is pressurized in a known manner to force the restriction into the arterial wall where the substance of the restruction can be absorbed over time.

Figure 3:
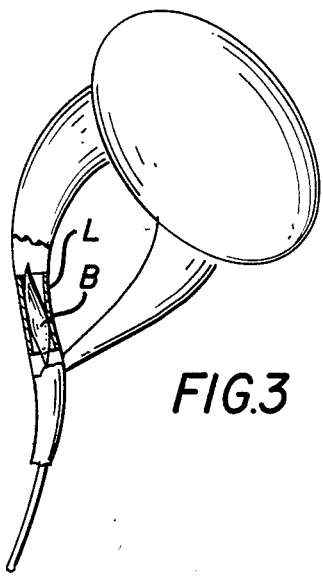
FIG. 3 is a diagrammatic view illustrating a sleeve in place in an artery and expanded into engagement with the arterial wall by a balloon catheter.

As seen in FIG. 3, a balloon catheter B is employed to position the sleeve or liner L in place. This procedure can be used in combination with a wire guide for the balloon catheter. The balloon catheter, with the liner thereon is moved through the arterial system to the location where the sleeve is to be placed. Then, upon inflation of the balloon, the liner will be pressed firmly against the inner wall of the artery. Upon deflation of the balloon it can then be removed, leaving the liner in place where it will remain under the influence of internal blood pressure.

Various modes of causing the liner to move through the arteries on the catheter are possible, including releasable mechanical connections or friction means responsive to interfacial contact of the balloon and the sleeve.

With the sleeve in place it is contemplated that stenosis will not as readily recur in the same region, as has heretofore been the general case.

We claim:

1. The method of inhibiting recurrence of stenosis in the coronary arterial system in the region of a treated stenosis, comprising moving a thin-walled elastic liner substantially conforming to the internal blood vessel wall into a location within the stenotic blood vessel region with said liner disposed on a balloon of a catheter, expanding the balloon to force the liner into engagement with the blood vessel wall, deflating the catheter and removing the catheter from the blood vessel, leaving the liner in place in said location.

* * * * *